(12) United States Patent
Köhler et al.

(10) Patent No.: US 9,971,003 B2
(45) Date of Patent: May 15, 2018

(54) ACCELERATED MAGNETIC RESONANCE THERMOMETRY

(75) Inventors: Max Oskar Köhler, Espoo (FI); Erkki Tapani Vahala, Hyvinkaa (FI); Kirsi Ilona Nurmilaukas, Vantaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 760 days.

(21) Appl. No.: 14/005,060

(22) PCT Filed: Mar. 2, 2012

(86) PCT No.: PCT/IB2012/050986
§ 371 (c)(1),
(2), (4) Date: Sep. 13, 2013

(87) PCT Pub. No.: WO2012/123846
PCT Pub. Date: Sep. 20, 2012

(65) Prior Publication Data
US 2014/0005523 A1    Jan. 2, 2014

(30) Foreign Application Priority Data

Mar. 17, 2011    (EP) .................................. 11158606

(51) Int. Cl.
*A61B 5/00*        (2006.01)
*G01R 33/48*       (2006.01)
(Continued)

(52) U.S. Cl.
CPC .......... *G01R 33/4804* (2013.01); *A61B 5/055* (2013.01); *A61B 18/02* (2013.01);
(Continued)

(58) Field of Classification Search
CPC ............................ G01R 33/4804; A61B 5/055
See application file for complete search history.

(56) References Cited

U.S. PATENT DOCUMENTS 6,194,899 B1 *  2/2001  Ishihara ............. G01R 33/4804
                                                        324/315
6,292,683 B1 *  9/2001  Gupta et al. ................... 600/410
(Continued)

FOREIGN PATENT DOCUMENTS

EP    1649806 A1    4/2006
WO    2010122449 A1  10/2010

OTHER PUBLICATIONS

Kuroda, K. et al "Temperature Mapping using the Water Proton Chemical Shift: Self-Referenced Method with Echo-Planar Spectroscopic Imaging" Magnetic Resonance in Medicine, vol. 43, 2000, pp. 220-225.

(Continued)

*Primary Examiner* — Tse Chen
*Assistant Examiner* — Joanne Hoffman

(57) ABSTRACT

A medical apparatus (300, 400, 500, 600) comprising a magnetic resonance imaging system (302). The medical apparatus further comprises a memory (332) storing machine readable instructions (352, 354, 356, 358, 470, 472, 474) for execution by a processor (326). Execution of the instructions causes the processor to acquire (100, 202) spectroscopic magnetic resonance data (334). Execution of the instructions further cause the processor to calculate (102, 204) a calibration thermal map (336) using the spectroscopic magnetic resonance data. Execution of the instructions further causes the processor to acquire (104, 206) baseline magnetic resonance thermometry data (338). Execution of the instructions further causes the processor to repeatedly acquire (106, 212) magnetic resonance thermometry data (340). Execution of the instructions further cause the processor to calculate (108, 214) a temperature map (351) using the magnetic resonance thermometry data, the calibration (Continued)

thermal map, and the baseline magnetic resonance thermometry data.

20 Claims, 8 Drawing Sheets

(51) Int. Cl.
*A61B 5/055* (2006.01)
*A61B 18/02* (2006.01)
*A61B 18/12* (2006.01)
*A61B 18/18* (2006.01)
*A61B 18/20* (2006.01)
*A61B 17/00* (2006.01)
*A61B 18/00* (2006.01)
*A61N 7/02* (2006.01)
*A61N 7/00* (2006.01)
*A61B 90/00* (2016.01)

(52) U.S. Cl.
CPC ......... *A61B 18/12* (2013.01); *A61B 18/1815* (2013.01); *A61B 18/20* (2013.01); *A61B 2017/00084* (2013.01); *A61B 2018/00791* (2013.01); *A61B 2090/374* (2016.02); *A61N 7/02* (2013.01); *A61N 2007/0065* (2013.01); *G01R 33/4808* (2013.01); *G01R 33/4814* (2013.01)

(56) References Cited

U.S. PATENT DOCUMENTS

| | | | | |
|---|---|---|---|---|
| 6,377,834 | B1* | 4/2002 | Zhou | G01R 33/4804 324/315 |
| 6,445,183 | B1* | 9/2002 | Shimizu | A61B 5/055 324/309 |
| 6,522,142 | B1* | 2/2003 | Freundlich | 324/315 |
| 2003/0130711 | A1* | 7/2003 | Pearson | A61B 18/1477 607/101 |
| 2004/0041563 | A1* | 3/2004 | Lewin et al. | 324/307 |
| 2004/0166062 | A1* | 8/2004 | Roberts et al. | 424/9.3 |
| 2005/0052183 | A1* | 3/2005 | Paliwal et al. | 324/315 |
| 2005/0163375 | A1* | 7/2005 | Grady | 382/180 |
| 2005/0206380 | A1* | 9/2005 | Seeber | 324/315 |
| 2006/0064002 | A1* | 3/2006 | Grist | A61B 5/055 600/410 |
| 2006/0206105 | A1* | 9/2006 | Chopra et al. | 606/27 |
| 2007/0106157 | A1* | 5/2007 | Kaczkowski et al. | 600/438 |
| 2007/0293753 | A1* | 12/2007 | El-Sharkawy et al. | 600/412 |
| 2008/0238423 | A1* | 10/2008 | Li et al. | 324/309 |
| 2008/0243112 | A1* | 10/2008 | De Neve | A61F 7/123 606/28 |
| 2009/0105581 | A1* | 4/2009 | Widenhorn | 600/411 |
| 2009/0160440 | A1* | 6/2009 | Yui | G01R 33/561 324/307 |
| 2009/0227859 | A1 | 9/2009 | Pile-Spellman | |
| 2009/0275821 | A1 | 11/2009 | Mallozzi | |
| 2010/0185080 | A1 | 7/2010 | Myhr | |
| 2010/0268065 | A1 | 10/2010 | Pile-Spellman | |
| 2011/0046472 | A1 | 2/2011 | Schmidt | |
| 2011/0046475 | A1 | 2/2011 | Assif | |

OTHER PUBLICATIONS

Weis, Jan et al "Noninvasive Monitoring of Brain Temperature during Mild Hypothermia", Sciencedirect Magnetic Resonanced Imaging, vol. 27, 2009 pp. 923-032.

Rieke, Viola et al "MR Thermometry", Journal of Magnetic Resonance Imaging, vol. 27, 2008, pp. 376-390.

Pan, Xinyi et al "Model-Based PRFS Thermometry using Fat as the Internal Reference and the Extended Prony Algorithm for Model Fitting", Sciencedirect Magnetic Resonance Imaging, vol. 28, 2010, pp. 418-426.

Siegler, P. et al "Temperature Effect in High Intensity Focused Ultrasound Therapy Control using Dynamic MR Elastography", Proc. Intl. Soc. Mag. Reson. Med. vol. 13, 2005, p. 2363.

* cited by examiner

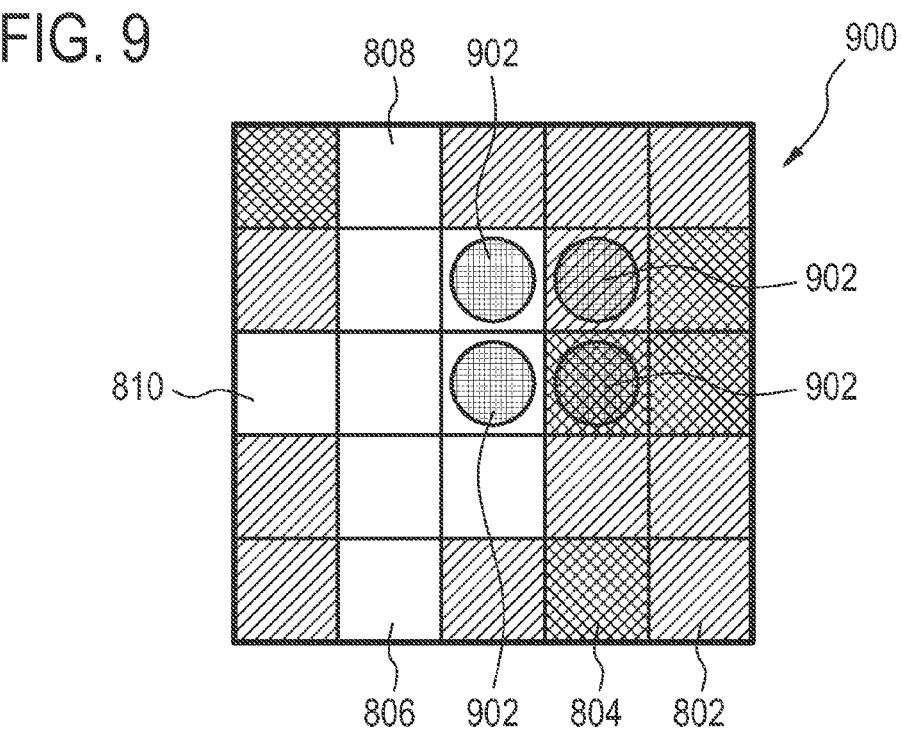

ACCELERATED MAGNETIC RESONANCE THERMOMETRY

CROSS-REFERENCE TO PRIOR APPLICATIONS

This application is the U.S. National Phase application under 35 U.S.C. § 371 of International Application No. PCT/IB2012/050986, filed on Mar. 2, 2012, which claims the benefit of European Patent Application No. 11158606.1, filed on Mar. 17, 2011. These applications are hereby incorporated by reference herein.

TECHNICAL FIELD

The invention relates to magnetic resonance imaging, in particular the measurement of temperatures using magnetic resonance imaging.

BACKGROUND OF THE INVENTION

In recent years magnetic resonance thermometry has been coupled with various means of heating or cooling tissue for therapy. Measuring the effect of the tissue heating or cooling allows the guiding of the therapy and also the ability to assess the effect of a therapeutic treatment on a subject.

In high-intensity focused ultrasound (HIFU) therapy, reliable real-time temperature monitoring using e.g. Magnetic Resonance Imaging (MRI) is necessary to ensure a sufficient thermal necrosis to the target while avoiding excessive heating and damage of surrounding healthy tissues. To achieve sufficient temporal and spatial resolution, fast imaging is required preferably with a high spatial resolution while maintaining a sufficient SNR for reconstruction of reliable temperature measurements.

In Rieke and Pauly, "MR Thermometry," J. Magn. Reson. Imaging, vol 27, (2008), pp. 376-390, the basic techniques of magnetic resonance thermometry are reviewed. This article also briefly discusses the combination of $T_1$ and Proton Resonant Frequency (PRF) MR thermometry techniques.

SUMMARY OF THE INVENTION

The invention relates to a medical apparatus, a method, and a computer program product in the independent claims. Embodiments are given in the dependent claims.

There are several different methods to measure temperature by utilizing magnetic resonance imaging. The proton resonance frequency (PRF) based temperature mapping method is commonly used because of its possibility to produce rapidly and precisely continuous temperature maps with high signal to noise ratio from the object or tissue in interest. The weakness of the method is that it does not give absolute temperature, but the temperature change relative to a certain, supposedly known initial state. Another method, the proton spectroscopic (PS) temperature imaging method, produces temperature maps with absolute temperature scale, but the method is too slow to be used in continuous imaging for most applications. Embodiments of the invention may combine the two methods, Proton frequency based temperature mapping and proton spectroscopic imaging temperature mapping methods, in such a way that the spectroscopic imaging is used for obtaining an initial guess and/or sanity checks during/before/after measuring temperature maps with the PRF method.

Water proton resonance frequency based temperature mapping method is based on the property of the water proton nuclei that the local magnetic field experienced by the nuclei depends linearly on the temperature at least in the temperature range 20-80° C. This causes the phase of the nuclei to depend linearly on their temperature on the RF-spoiled gradient echo images. The formula used for calculation is:

$$\Delta T = T - Tref = (\varphi(T) - \varphi(T_{ref}))/(\alpha \gamma T_E B_0),$$

where $\varphi$ is the phase image at temperature $T$ and $T_{ref}$, $\alpha$ is the water chemical shift in ppm*° $C.^{-1}$, $\gamma$ is the proton gyromagnetic ratio, $T_E$ is the echo time and $B_0$ is the main magnetic field. The method is almost independent of tissue composition.

Proton spectroscopic imaging based temperature mapping method can produce temperature maps on absolute scale. The method relies on the same physical principles of water proton resonance shift temperature dependence as the PRF method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU treatment as opposed to using a spatially homogeneous starting temperature taken as the body core temperature measured with a thermometer probe, which is current practice. Alternatively, the PS method can be used as a sanity check for cumulated temperature between treatment heatings outside treatment area.

An alternative method to the conventional proton spectroscopic imaging in obtaining absolute scale temperature maps is to use dual- or multi-echo sequences, for example fast field echo (FFE) sequences. The PRF shift of water protons is obtained by comparing their echo to a reference tissue echo, which is expected to remain at unchanged position with temperature. For example, a least squares fit can be made on the echo data to obtain reliable estimates. The method can be considerably faster than the conventional spectroscopic method, but can suffer from echoes from other sources than water and reference tissue in the same voxel. This method could also be combined with the PRF method in the same use as the Proton spectroscopic method described above.

Both methods, the PRF and PS method suffer from different weaknesses. Combining the two methods, the weaknesses could be mitigated and more reliable temperature measurements could be performed.

Proton resonance frequency based method is used for example in medical applications of magnetic resonance imaging. One example is the Magnetic Resonance Guided High Intensity Focused Ultrasound therapy to determine the temperature of the tissue under interest. The PRF method is well suited for continuous imaging, but has the drawback that it does not give the absolute temperature, but only a temperature relative to the initial state. If, for example, the initial state differs from the expected initial state, or other changes affecting the phase of the investigated protons occur during the measurement or between the measurements, there can be large errors in the temperatures obtained with the method and the estimate of the induced thermal damage. On the other hand, the PS method produces absolute scale temperature maps but it is too slow for continuous imaging. Also, changes can occur in temperature during the long acquisition time. Therefore, the method is not suitable for using alone in the MR-HIFU therapy. If the two methods, PRF and PS methods, are combined in such a way that the PRF method is used for continuous measurement during MR-HIFU sonication and the PS method is used for measuring for example the initial state and/or checks in between or after the PRF measurements made during sonication, the temperature measurement method could be made more reliable.

The usage of two different temperature mapping methods (PRF and PS methods) in combination to take advantage of the good properties of each and to overcome problems concerning each method.

Both methods, PRF and PS based methods, are already established temperature measurement methods on their own. One example of possible usage the innovation is with MR-HIFU therapy. The PRF method is used as standard temperature mapping tool in that application. The temperature is measured at about 3 s intervals and the ultrasound heating of about 30 s is repeated in about 3 minutes intervals. In a first approximation it may be assumed that the initial temperature in the human body is constant everywhere. It may also be assumed that the temperature of tissue outside the heating area returns to the initial state in the waiting time between successive ultrasound heatings. These two assumptions are, however, never entirely correct. The temperature distribution in the initial state and in between or during heating events (outside the heating area) can be directly measured by using PS method and the resulting temperature maps can be used as an initial state for the next PRF temperature measurement.

Any application that uses the PRF method for temperature measurement, for example of human or animal tissue or any other material, can be combined with the PS method to allow initial estimates or sanity checks to be performed before/during/after the PRF measurement. For example, PRF temperature mapping is used in Magnetic Resonance Guided High Intensity Focused Ultrasound therapy for monitoring the temperature of the target and surrounding tissue before, during and after ultrasound ablation. The PS method could be utilized to obtain a more accurate estimate for the initial temperature map of the tissue and the PRF method can then be used to track temperature changes to the measured initial state. Also, checks can be made with the PS method during or after heating the tissue with ultrasound. The combination can be automatic or the temperature maps can be provided to the user for visual analysis without any further computed processing.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

MR thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' as used herein encompasses to any device comprising a processor. A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

In one aspect the invention provides for a medical apparatus comprising a magnetic resonance imaging system for acquiring magnetic resonance data. The medical apparatus further comprises a processor for controlling the medical apparatus. The medical apparatus further comprises a memory containing machine-readable instructions for execution by the processor. Execution of the machine-readable instructions causes the processor to acquire spectroscopic magnetic resonance data. Spectroscopic magnetic resonance data as used herein encompasses magnetic resonance data which comprises information about more than one resonance peak.

Execution of the instructions further cause the processor to calculate a calibration thermal map using the spectroscopic magnetic resonance data. If a voxel contains certain types of tissue for instance adipose or fatty tissue then a spectroscopic method may be used to determine the absolute temperature within that voxel. However, the acquisition of spectroscopic magnetic resonance data for an entire slice or volume is time consuming. Execution of the machine-readable instructions further cause the processor to acquire baseline magnetic resonance thermometry data. The baseline magnetic resonance thermometry data is simply a label for magnetic resonance thermometry data which is used as a reference to the calibration thermal map. The techniques which were previously outlined as being useful for determining temperature using magnetic resonance thermometry operate by noting the change in various parameters or parameter. The baseline magnetic resonance thermometry data may therefore be used as a reference measurement against the calibration thermal map.

Execution of the instructions further cause the processor to repeatedly acquire magnetic resonance thermometry data. Execution of the machine executable instructions further cause the processor to also repeatedly calculate a temperature map using the magnetic resonance thermometry data, the calibration thermal map, and the baseline magnetic resonance thermometry data.

This embodiment is advantageous because it combines the accuracy of performing spectroscopic measurements to determine the absolute temperature with the speed of other temperature measurement techniques. For instance the proton resonance frequency shift method of measuring temperature is extremely fast. However, it only measures a relative change in temperature. The claimed apparatus first takes an accurate spectroscopic measurement of the absolute temperature and then uses another relative technique to rapidly acquire and construct a temperature map.

In another embodiment the medical apparatus further comprises a temperature treatment system for treating a target volume of a subject. During acquisition of the magnetic resonance thermometry data execution of the instructions further cause the processor to generate temperature treatment system commands in accordance with the temperature map. In some embodiments a treatment plan may also be used to generate the temperature treatment system commands. The temperature treatment system commands cause the temperature treatment system to treat the target zone. For instance the temperature treatment system commands may be commands or instructions for operating the temperature treatment system. The temperature map may be used to determine which regions of a subject are being heated by the temperature treatment system. By using the temperature map to generate the temperature treatment system commands a feedback and control loop is in essence created. A treatment plan as used herein encompasses a description or instructions for performing a therapy. In this case a treatment plan would be for the heating of the target volume of the subject. The medical apparatus may for instance have a software module which takes as input the temperature map and/or a treatment plan and then is able to generate commands for controlling the temperature treatment system. Execution of the machine-executable instructions further cause the processor to send the temperature treatment system commands to the temperature treatment system. By sending the temperature treatment system commands to the temperature treatment system this in effect causes the temperature treatment system to treat the target volume.

In another embodiment execution of the instructions further cause the processor to generate pause commands which cause the temperature treatment system to pause treatment of the target zone for a predetermined period of time. For instance a high-intensity focused ultrasound system may heat for a period of time and then wait for a period of time before continuing to heat. This may be necessary to allow the skin and other healthy tissue between the target and transducer to cool down. The pause commands as used herein are again commands which are capable of controlling the temperature treatment system. The pause commands specifically cause the temperature treatment system to pause or halt the temperature treatment of the target volume. Execution of the machine-readable instructions further cause the processor to send the pause commands to the temperature treatment system. Execution of the machine executable instructions further cause the processor to re-acquire the spectroscopic magnetic resonance data during the predetermined period of time.

Execution of the instructions further cause the processor to re-calculate the calibration thermal map using the spectroscopic magnetic resonance data. Execution of the instructions further cause the processor to re-acquire the baseline magnetic resonance thermometry data. This embodiment is particularly advantageous because over an extended period of time the temperature map may become increasingly inaccurate. Essentially anything which affects the magnetic resonance measurements may do this. For instance there may be $B_0$ drift in the magnetic field, the gradient fields may heat and may change the magnetic field that they generate, and there may also be other components which heat or change during the process which cause a change in the magnetic resonance thermometry data that is unrelated to a temperature change within the subject. This embodiment is particularly advantageous when performing PRF thermometry over multiple consecutive heating events, e.g., measuring the temperature change induced by all heating events from the first till the current. This cumulative thermometry requires correction methods to be used to remove the effect of mechanically moving the heat applicator between the heating events as is needed in for example HIFU therapy. This motion of the applicator typically causes susceptibility changes and consequently PRF thermometry artifacts if not compensated. Such compensation is typically imperfect and may over time lead to substantial additional temperature artifacts.

While the temperature treatment system is paused during the predetermined period of time the magnetic resonance imaging system is used to re-acquire the spectroscopic magnetic resonance data and baseline magnetic resonance thermometry data such that a new calibration thermal map may be created. This is particularly beneficial when a therapy performed with the medical apparatus is of a long duration.

In another embodiment the temperature treatment system is a high-intensity focused ultrasound system.

In another embodiment the temperature treatment system is a radio-frequency tissue treating system. For instance a radio-frequency antenna may be used to heat the target volume using radio-frequency energy. Typically an additional antenna is used or placed in the vicinity of the subject to generate the radio-frequency energy that heats the target zone.

In another embodiment the temperature treatment system is a microwave applicator. A microwave applicator is adapted for directing microwave energy at the target zone. This may cause an increase in temperature of the target zone.

In another embodiment the temperature treatment system is a cryo-ablator. A cryo-ablator is adapted for cooling the target zone or a portion of the target zone to temperatures which cause the ablation of tissue.

In another embodiment the temperature treatment system is a laser. The laser may be used to selectively ablate tissue.

In another embodiment the temperature treatment system commands are generated in accordance with a treatment plan.

In another embodiment the temperature treatment system commands are generated in accordance with the temperature map.

In another embodiment the temperature treatment system commands are generated in accordance with both the treatment plan and the temperature map.

In another embodiment execution of the machine-readable instructions further cause the processor to identify voxels of the calibration thermal map which lack spectroscopic thermal magnetic resonance data for calculating the thermal map. Execution of the instructions further causes the processor to extrapolate the thermal map into the identified voxels. In order to use a spectroscopic method to absolutely calibrate the temperature within a voxel the presence of certain types of tissue need to be there. For instance if there is fatty or adipose tissue measurements can be made of both the water and protons tied to fat or oil molecules in order to determine the temperature absolutely. Within some voxels however there may not be tissue which is able to be used for the calibration. A normal solution to this would be to simply assume that all the voxels have the same starting temperature. This assumption is incorrect when the temperature within the subject is non-uniform, which it always is to at least some degree. For instance, if the subject had just undergone heating then it would be expected that the temperature within the subject would be very non-uniform. This is a particularly advantageous embodiment because it allows the construction of a calibration thermal map when the temperature within the subject is non-uniform.

In another embodiment the thermal map is extrapolated and/or refined using a thermal model of the subject. For instance there may be different tissue types within the subject. By knowing the properties of these various tissue types a thermal model can be used which may be able to accurately reconstruct the temperature in the identified voxels. In some embodiments an interpolation may first be performed to use as a seed value for the model. Using a model to refine a temperature estimate made by interpolation may be useful to eliminate unphysical temperature changes from one voxel to the next.

In another embodiment execution of the machine executable instructions further causes the processor to construct the thermal model using the spectroscopic magnetic resonance data. For instance the data acquired with the spectroscopic magnetic resonance data may be sufficient to determine the tissue type in each voxel. This may be used to construct the thermal model.

When a thermal model is used to calculate the temperature it for instance may be a finite difference type model or it may also be something similar to a lumped elements model. Essentially the heat flow across a boundary between each individual voxel can be modeled.

In another embodiment the medical apparatus further comprises a temperature treatment system for treating a target volume of a subject. Execution of the machine-executable instructions further causes the processor to treat the target volume during acquisition of the magnetic resonance thermometry data. Treatment of the target model is modeled by the thermal model. For instance the temperature treatment system may cause a known amount of heat to be added or withdrawn from particular voxels. This may be used in conjunction with the thermal model to more accurately determine the temperature within the identified voxels.

In another embodiment the thermal map is extrapolated by interpolating the temperature in the identified voxels. In this embodiment instead of using a complex model the temperature map is simply performed by interpolating the temperature in the identified voxels. This may be useful in a situation where a more complex thermal model is not available or is not able to be constructed. This however would still be more accurate than assuming that the temperature within the subject is uniform. Performing an interpolation may also be beneficial when the interpolated values are used as an initial value or seed value for a model calculation.

In another embodiment the magnetic resonance thermometry data comprises proton density data.

In another embodiment the magnetic resonance thermometry data comprises T1 relaxation time data.

In another embodiment the magnetic resonance thermometry data comprises T2 relaxation time data.

In another embodiment the magnetic resonance thermometry data comprises T2-star relaxation time data.

In another embodiment the magnetic resonance thermometry data comprises diffusion coefficient data.

In another embodiment the magnetic resonance thermometry data comprises proton-resonance frequency shift data.

In another embodiment the magnetic resonance thermometry data comprises combinations of the aforementioned possibilities of what the magnetic resonance thermometry data could be.

In another embodiment the spectroscopic magnetic resonance data is descriptive of the proton-resonance frequency shift of multiple resonance peaks. The multiple resonance peaks are used to be able to identify the temperature absolutely. Some proton-resonance frequency shifts are not very sensitive to temperature and others are extremely sensitive. By comparing two peaks with a different temperature sensitivity the absolute temperature within a voxel may be calculated or determined.

In another aspect the invention provides for a method of operating a medical apparatus. Likewise the invention also provides for a computer-implemented method of operating a medical apparatus. The apparatus comprises a medical resonance imaging system for acquiring magnetic resonance data. The method comprises the step of acquiring spectroscopic magnetic resonance data. The method further comprises the step of calculating a calibration thermal map using the spectroscopic magnetic resonance data. The method further comprises the step of acquiring baseline magnetic resonance thermometry data. The method further comprises the step of repeatedly acquiring magnetic resonance thermometry data. The method further comprises repeatedly performing the step of calculating a temperature map using the magnetic resonance thermometry data. The method further comprises repeatedly calculating a temperature map using the magnetic resonance thermometry data, the calibration thermal map, and the baseline magnetic resonance thermometry data.

In another aspect the invention provides for a computer program product comprising machine-executable instructions for controlling a medical apparatus. For instance the computer program product may be stored on a computer-readable storage medium. The medical apparatus comprises a magnetic resonance imaging system for acquiring magnetic resonance data. The medical apparatus further comprises a processor for executing the instructions. Execution of the instructions causes the processor to acquire spectroscopic magnetic resonance data. Execution of the instructions further causes the processor to calculate a calibration thermal map using the spectroscopic magnetic resonance data. Execution of the instructions further causes the processor to acquire baseline magnetic resonance thermometry data. Execution of the instructions further causes the processor to repeatedly acquire magnetic resonance thermometry data. Execution of the machine-executable instructions further cause the processor to calculate a temperature map using the magnetic resonance thermometry data, the calibration thermal map, and the baseline magnetic resonance thermometry data.

BRIEF DESCRIPTION OF THE DRAWINGS

In the following preferred embodiments of the invention will be described, by way of example only, and with reference to the drawings in which:

FIG. 9 is a graph which is used to illustrate a further method of extrapolating the temperature in voxels in a calibration thermal map.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
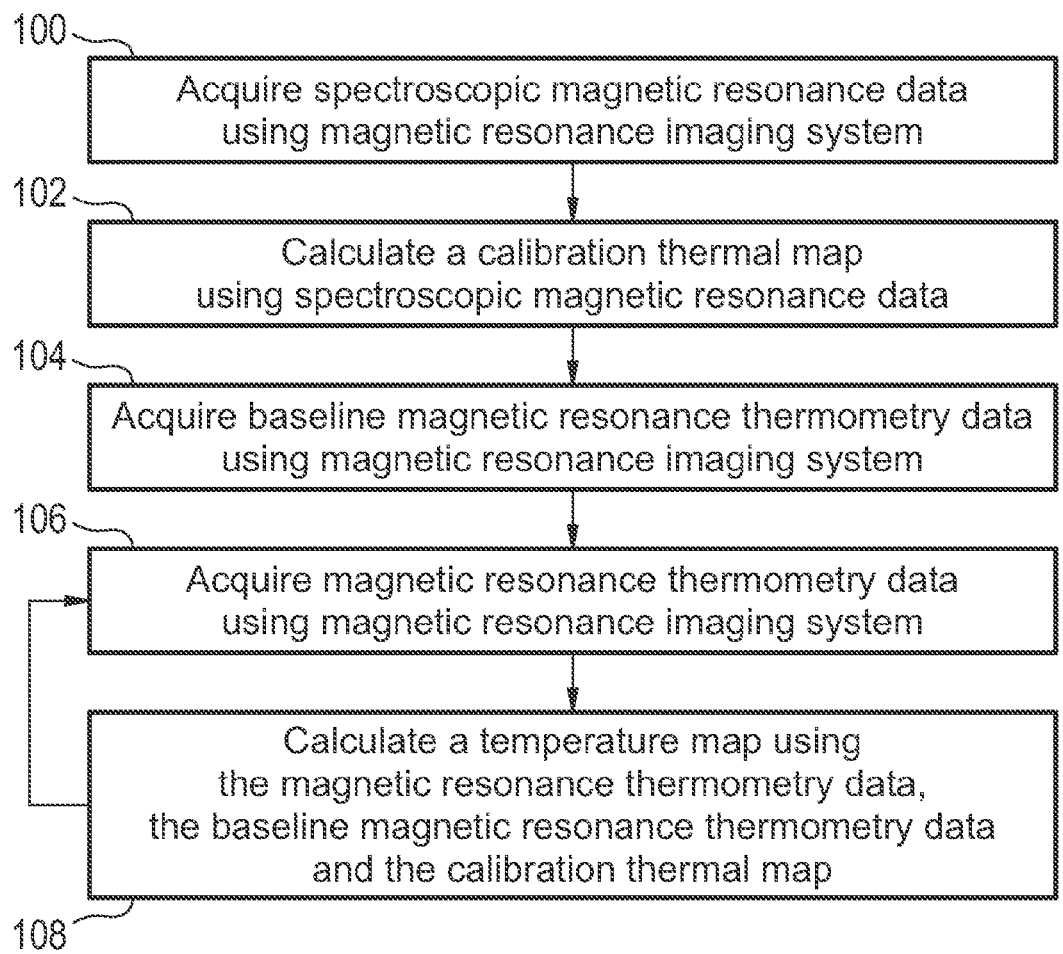
FIG. 1 shows a flow diagram which illustrates a method according to an embodiment of the invention.

FIG. 1 shows a flow diagram which illustrates a method according to an embodiment of the invention. First in step 100 spectroscopic magnetic resonance data is acquired using a magnetic resonance imaging system. In step 102 a calibration thermal map is calculated using the spectroscopic magnetic resonance data. In step 104 baseline magnetic resonance thermometry data is acquired using the magnetic resonance imaging system. The baseline magnetic resonance thermometry data may be used to create a baseline set of measurements for comparison to the calibration thermal map. Next in step 106 magnetic resonance thermometry data is acquired using the magnetic resonance imaging system. In step 108 a temperature map is calculated using the magnetic resonance thermometry data, the baseline magnetic resonance thermometry data, and the calibration thermal map. Steps 106-108 are repeated a number of times. The method shown in FIG. 1 allows accurate temperature maps to be acquired and calculated. The calibration thermal map is constructed using spectroscopic magnetic resonance data and is thus calibrated for absolute temperature. A more rapid method may be then used to calculate the temperature maps which are then related to the calibration thermal map by the magnetic resonance thermometry data.

Figure 2:
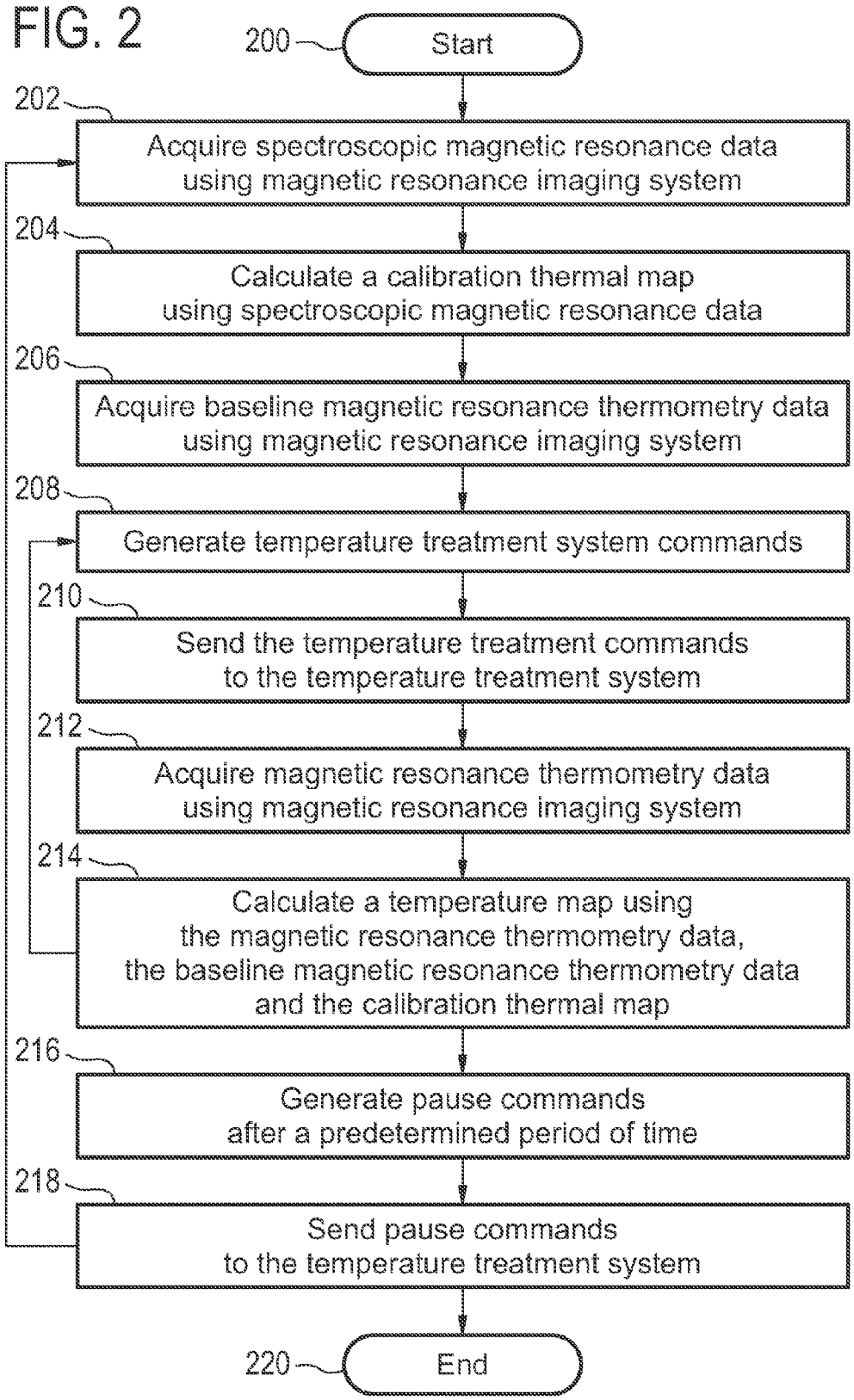
FIG. 2 shows a flow diagram which illustrates a method according to a further embodiment of the invention.

FIG. 2 shows a flow diagram which illustrates a method according to a further embodiment of the invention. In step 200 the method starts. Next in step 202 spectroscopic magnetic resonance data is acquired using a magnetic resonance imaging system. Next in step 204 a calibration thermal map is calculated using spectroscopic magnetic resonance data. In step 206 baseline magnetic resonance thermometry data is acquired using magnetic resonance imaging system. Next in step 208 temperature treatment system commands are generated. At this point the temperature treatment commands may be generated using a treatment plan. Next in step 210 the temperature treatment commands are sent to the temperature treatment system. This causes the temperature treatment system to treat a target zone of a subject. Next in step 212 magnetic resonance thermometry data is acquired using a magnetic resonance imaging system. Next in step 214 a temperature map is calculated using the magnetic resonance thermometry data, the baseline magnetic resonance thermometry data, and the calibration thermal map. Steps 208, 210, 212 and 214 may be repeated a number of times. Steps 208 and 210 may not be repeated during every iteration. That is to say the generating the temperature treatment system commands and sending them to the temperature treatment system may or may not be performed with every loop of steps 208-214.

After a temperature map has been calculated then the temperature treatment system commands may be generated using the temperature map and/or information from the treatment plan. Calculating the temperature map and then generating the temperature treatment system commands using the temperature map forms a feedback loop where the magnetic resonance imaging system is used to monitor the temperature of the subject and adjust the treatment of the target zone accordingly. Periodically pause commands are generated after a predetermined period of time, this is box 216. After the pause commands have been generated then the pause commands are sent to the temperature treatment system 218 and this causes the system to pause. During the pause the method restarts the step 202 where the spectroscopic magnetic resonance data is acquired again using the magnetic resonance imaging system, then step 204 is performed again as is step 206. This has the effect of creating a new calibration thermal map with a baseline magnetic resonance thermometry data. This is in a sense periodically re-calibrating the measurements. This has a great benefit during long therapy sessions. The method is then repeated iteratively until the method ends in step 220. Steps 216 and 218 are not necessarily repeated before the method ends at step 220.

Figure 3:
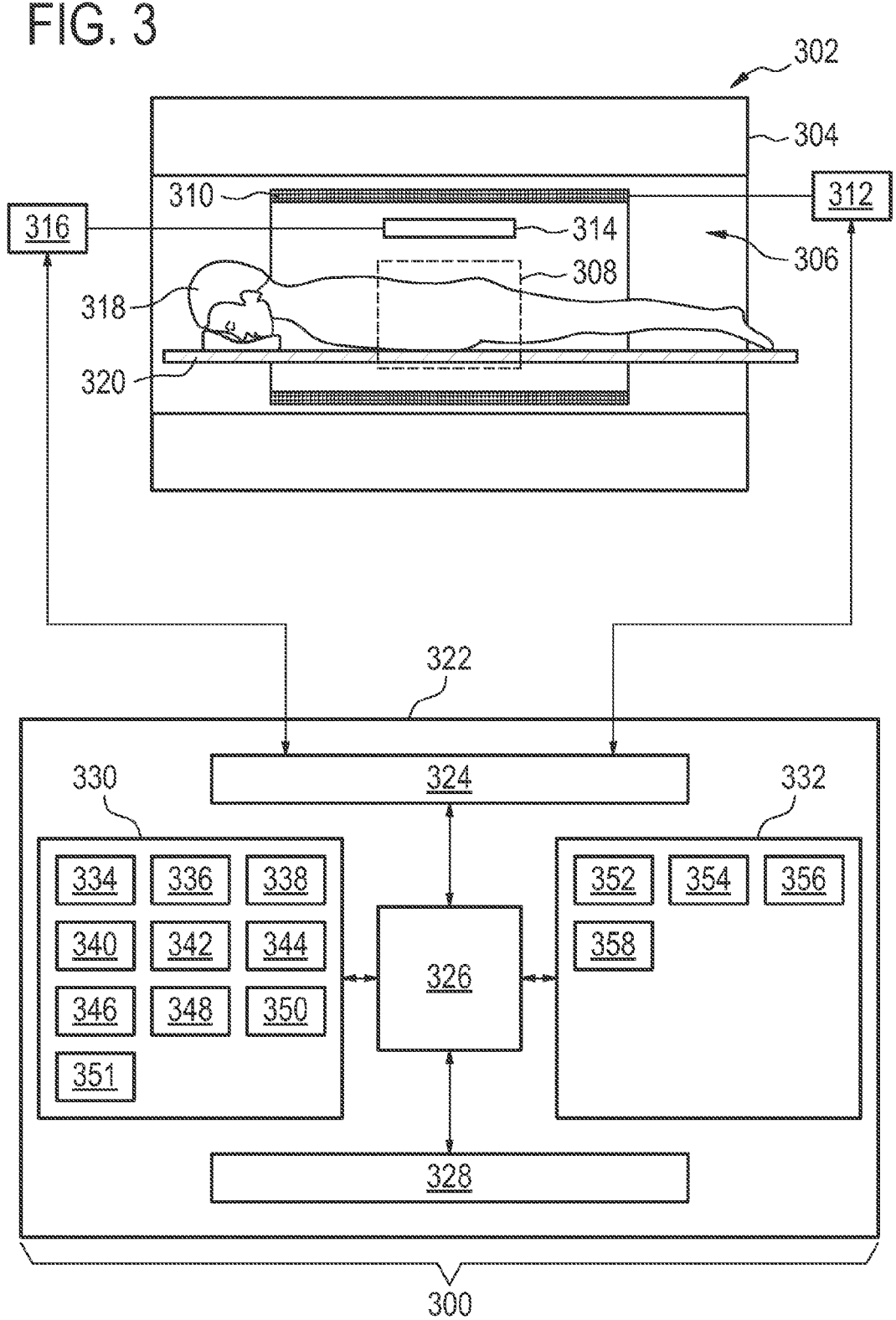
FIG. 3 shows an embodiment of a medical apparatus according to an embodiment of the invention.

FIG. 3 shows an embodiment of a medical apparatus 300 according to an embodiment of the invention. The medical apparatus 300 comprises a magnetic resonance imaging system 302. The magnetic resonance imaging system comprises a magnet 304. The magnet 304 is a cylindrical type superconducting magnet with a bore 306 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet there is an imaging zone 308 where the magnetic field is strong and uniform enough to perform magnetic resonance imaging.

Within the bore 306 of the magnet there is also a set of magnetic field gradient coils 310 which are used for acquisition of magnetic resonance data to spatially encode magnetic spins within the imaging zone 308 of the magnet 304. The magnetic field gradient coils are connected to a magnetic field gradient coil power supply 312. The magnetic field gradient coils 310 are intended to be representative. Typically magnetic field gradient coils contain three separate sets of coils for spatially encoding in three orthogonal spatial directions. A magnetic field gradient power supply 312 supplies current to the magnetic field gradient coils 310. The current supplied to the magnetic field coils is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone. The radio-frequency coil may contain multiple coil elements. The radio-frequency coil may also be referred to as a channel or an antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and receivers.

A subject 318 is shown as reposing on a subject support 320 and is located partially within the imaging zone 308. The magnetic field gradient coil power supply 312 and the transceiver 316 are connected to a hardware interface 324 of a computer system 322. The computer system 322 also comprises a processor 326 which is connected to the hardware interface 324. The hardware interface 324 enables the processor 326 to send and receive messages from the rest of the medical apparatus 300. The processor 326 controls the medical apparatus 300 via the hardware interface 324. The computer system 322 is also shown as comprising a user interface 328, computer storage 330, and computer memory 332. All of these three are shown as being connected to the processor 326.

The computer storage 330 is shown as containing spectroscopic magnetic resonance data 334 acquired using the magnetic resonance imaging system 302. The computer storage 330 is further shown as containing a calibration thermal map 336. The calibration thermal map 336 was constructed using the spectroscopic magnetic resonance data 334. The computer storage 330 is further shown as containing baseline magnetic resonance thermometry data. The computer storage 330 is further shown as containing magnetic resonance thermometry data 340 also acquired using the magnetic resonance imaging system 302. The computer storage 330 is further shown as containing a spectroscopic pulse sequence 342. The spectroscopic pulse sequence 342 was used for acquiring the spectroscopic magnetic resonance data 334.

The computer storage 330 is further shown as containing magnetic resonance thermometry pulse sequence 344. The magnetic resonance thermometry pulse sequence 344 was used for acquiring the baseline magnetic resonance thermometry data 338 and the magnetic resonance thermometry data 340. The computer storage 330 is further shown as containing a proton density pulse sequence 346. The proton density pulse sequence 346 was used to acquire magnetic resonance data 348 which is also shown as being contained within the computer storage 330. The computer storage 330 is further shown as containing a magnetic resonance image 350 which was reconstructed from the magnetic resonance data 348. The magnetic resonance image 350 may be displayed and/or registered to the calibration thermal map 336 and a temperature map 351. The temperature map 351 is shown as being within the computer storage 330. The temperature map 351 was constructed using the calibration thermal map 336, the baseline magnetic resonance thermometry data 338 and the magnetic resonance thermometry data 340.

The computer memory 332 is shown as containing machine executable instructions 352, 354, 356 and 358 for operating the medical apparatus 300. Specifically the computer memory 332 is shown as containing a control module 352. The control module 352 contains machine executable instructions for controlling the operation and function of the medical apparatus 300. For instance the control module 352 may use any of the pulse sequences 342, 344, 346 to generate commands which allow the processor 326 to acquire magnetic resonance data and/or thermometry data using the magnetic resonance imaging system 302. The computer memory 332 is further shown as containing a calibration thermal map module 354. The calibration thermal map module 354 contains computer executable code which enables the processor 326 to calculate the calibration thermal map 336 using the spectroscopic magnetic resonance data 334. The computer memory 332 is shown as further containing a temperature map module 356. The temperature map module 356 contains computer executable code which allows the processor 326 to calculate the temperature map 351 using the calibration thermal map 336, the baseline magnetic resonance thermometry data 338, and the magnetic resonance thermometry data 340. The memory 332 is further shown as containing an image reconstruction module 358. The image reconstruction module contains computer executable code which enables the processor 326 to reconstruct the magnetic resonance image 350 from the magnetic resonance data 348.

Figure 4:
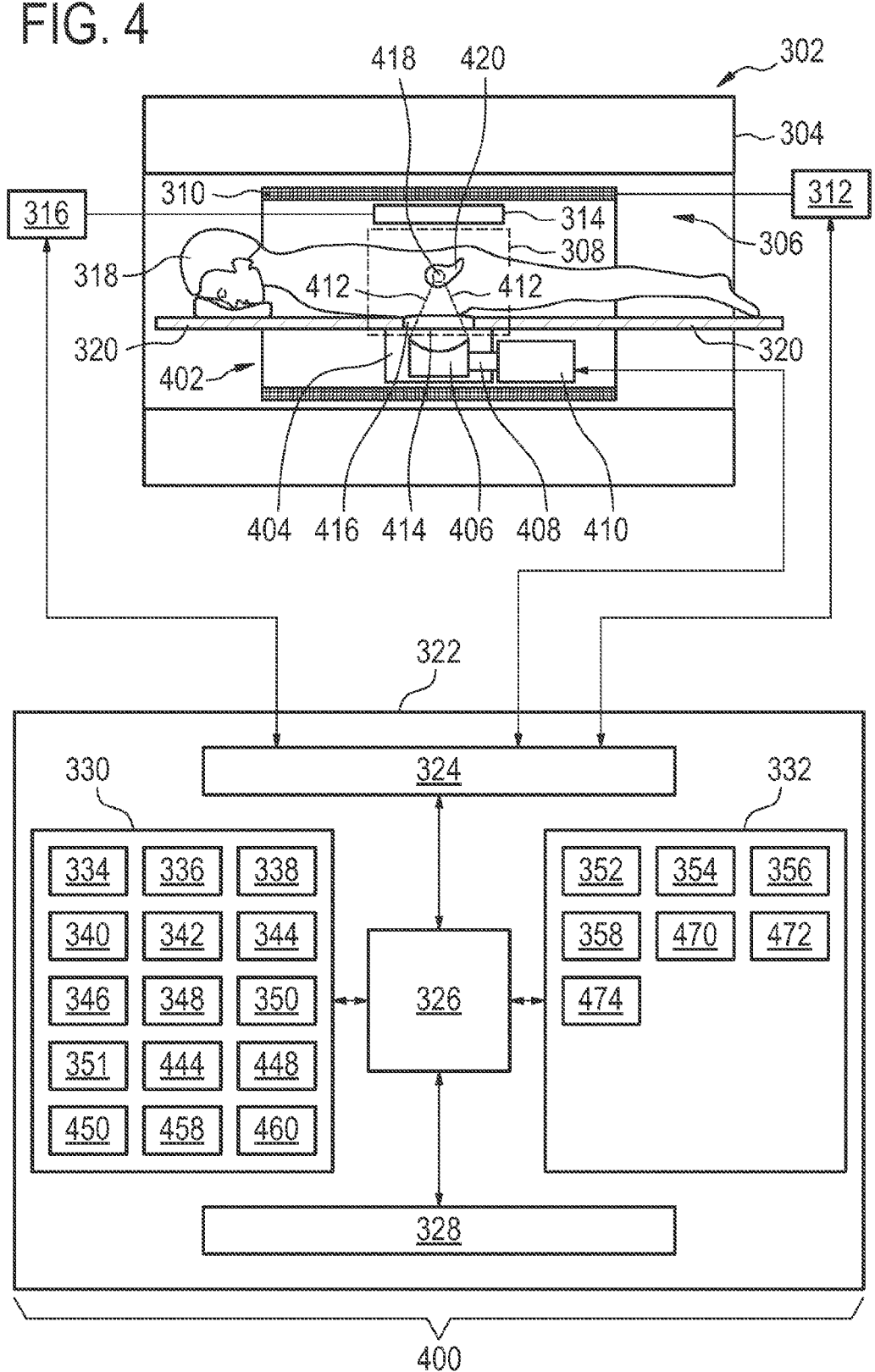
FIG. 4 shows an embodiment of a medical apparatus according to a further embodiment of the invention.

FIG. 4 illustrates a medical apparatus 400 according to a further embodiment of the invention. In addition to the components, the embodiment shown in FIG. 4 comprises a temperature treatment system which is a high-intensity focused ultrasound system 402. The high-intensity focused ultrasound system comprises a fluid-filled chamber 404. Within the fluid-filled chamber 404 is an ultrasound transducer 406. Although it is not shown in this figure the ultrasound transducer 406 may comprise multiple ultrasound transducer elements each capable of generating an individual beam of ultrasound. This may be used to steer the location of a sonication point 418 electronically by controlling the phase and/or amplitude of alternating electrical current supplied to each of the ultrasound transducer elements.

The ultrasound transducer 406 is connected to a mechanism 408 which allows the ultrasound transducer 406 to be repositioned mechanically. The mechanism 408 is connected to a mechanical actuator 410 which is adapted for actuating the mechanism 408. The mechanical actuator 410 also represents a power supply for supplying electrical power to the ultrasound transducer 406. In some embodiments the power supply may control the phase and/or amplitude of electrical power to individual ultrasound transducer elements. In some embodiments the mechanical actuator/power supply 410 is located outside of the bore 304 of the magnet 302.

The ultrasound transducer 406 generates ultrasound which is shown as following the path 412. The ultrasound 412 goes through the fluid-filled chamber 408 and through an ultrasound window 414. In this embodiment the ultrasound then passes through a gel pad 416. The gel pad is not necessarily present in all embodiments but in this embodiment there is a recess in the subject support 314 for receiving a gel pad 416. The gel pad 416 helps couple ultrasonic power between the transducer 406 and the subject 312. After passing through the gel pad 416 the ultrasound 412 passes through the subject 312 and is focused to a sonication point 418. The sonication point 418 is being focused within a target zone 420. The sonication point 418 may be moved through a combination of mechanically positioning the ultrasonic transducer 406 and electronically steering the position of the sonication point 418 to treat the entire target zone 420.

The high-intensity focused ultrasound system 402 is shown as being also connected to the hardware interference 324 of the computer system 322. The computer system 322 and the contents of its storage 330 and memory 332 are equivalent to that as shown in FIG. 3.

The computer storage 330 is further shown as containing a treatment plan 444. A treatment plan as used herein is either descriptive of or contains instructions for treating a target zone 420 of a subject 318. The computer storage 330 is further shown as containing temperature treatment system commands. The temperature treatment system commands 448 contain instructions that when sent to the high-intensity focused ultrasound system 402 cause it to heat the target zone 420. The computer storage 330 is further shown as containing pause commands 450. The pause commands 450 cause the temperature treatment system 402 to cease temperature treatment of the target zone 420 for a period of time. The computer storage 330 is further shown as containing identified voxels 458. The identified voxels 458 are voxels which lack spectroscopic magnetic resonance data for calibrating the thermal map. The computer storage 330 is further shown as containing a thermal model 460. The thermal model 460 may be used in some embodiments to calculate the temperature within the identified voxels 458.

The computer memory 332 is further shown as containing a temperature treatment system control module 470. The temperature treatment system control module 470 is adapted for generating the temperature treatment system commands 448 and the pause commands 450. The temperature treatment system control module 470 may use the treatment plan 444 and/or the temperature map 351 to generate the temperature treatment system commands 448 and/or the pause commands 450. The computer memory 332 is further shown as containing a voxel identification module. The voxel identification module contains computer-executable code which allows the processor 326 to identify the identified voxels 458 in the spectroscopic magnetic resonance data 334. The computer memory 332 is further shown as containing a temperature extrapolation module 474. The temperature extrapolation module contains computer-executable code for extrapolating the temperature within the identified voxels 458. In some embodiments a thermal model 460 may be used. In other models the temperature in the identified voxels 458 are simply interpolated.

Figure 5:
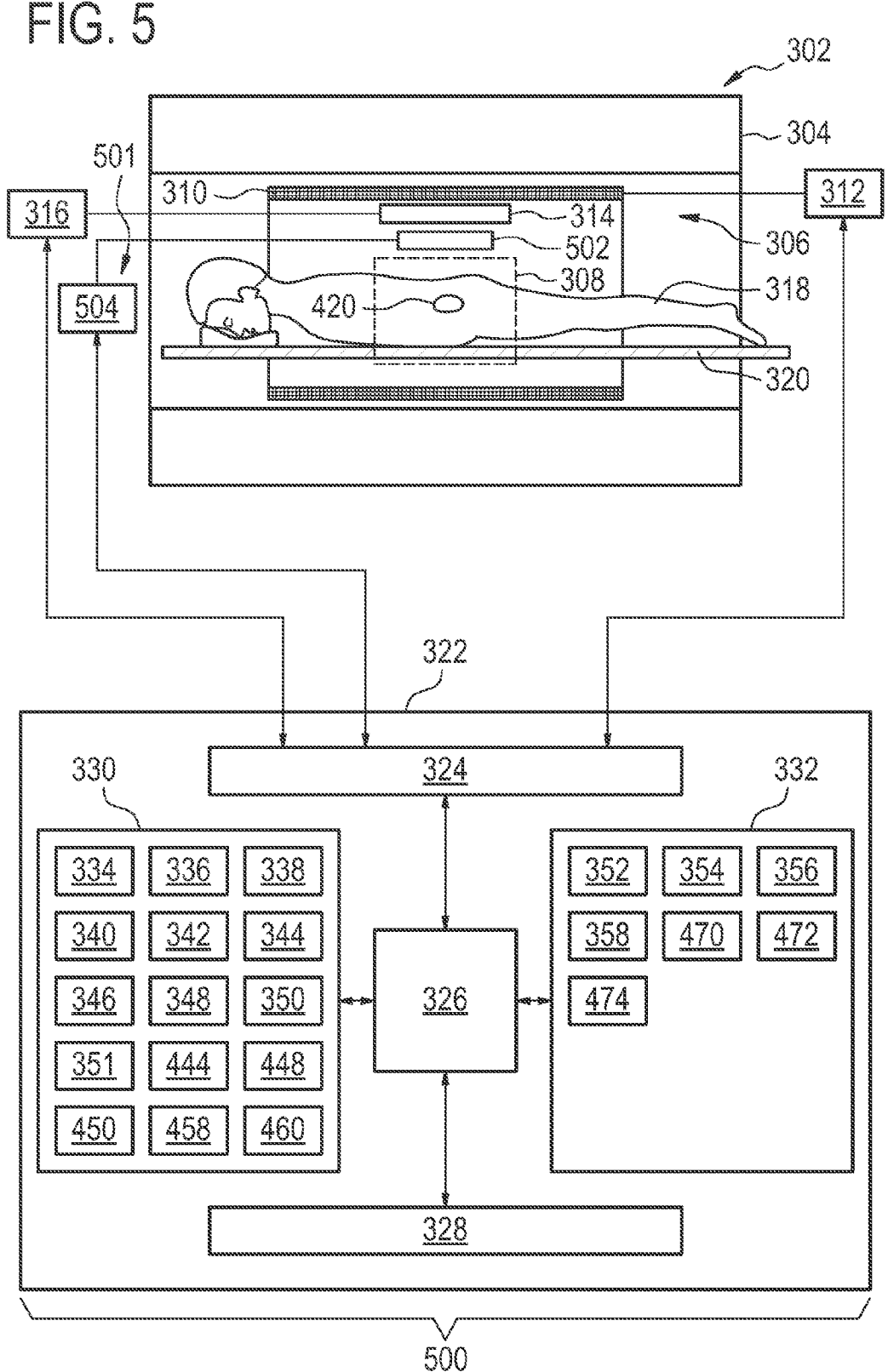
FIG. 5 shows an embodiment of a medical apparatus according to a further embodiment of the invention.

FIG. 5 shows a medical apparatus 500 according to a further embodiment of the invention. The embodiment shown in FIG. 5 is similar to that shown in FIGS. 3 and 4. The computer system 324 of FIG. 5 is equivalent to the computer system 324 shown in FIGS. 3 and 4 also. The contents of the computer storage 328 and the computer memory 330 are also equivalent to the computer storage 330 and the computer memory 332 as shown in FIGS. 3 and 4. In the embodiment shown in FIG. 5 a radio-frequency tissue heating system 501 is used as the temperature treatment system. The radio-frequency temperature treatment system 501 comprises an antenna 502 and a radio-frequency transmitter 504. The antenna 502 is in the vicinity of target zone 420. Radio-frequency energy generated by the transmitter 504 and radiated by the antenna 502 is used to selectively heat the target zone 420. In this embodiment the radio-frequency transmitter 504 is shown as being connected to the hardware interface 324. The processor 326 and the contents of the computer storage 330 and the computer memory 332 are used to control the radio-frequency transmitter 504 in a manner equivalent to the way the high-intensity focused ultrasound system 402 of FIG. 4 is controlled by the processor 326.

Figure 6:
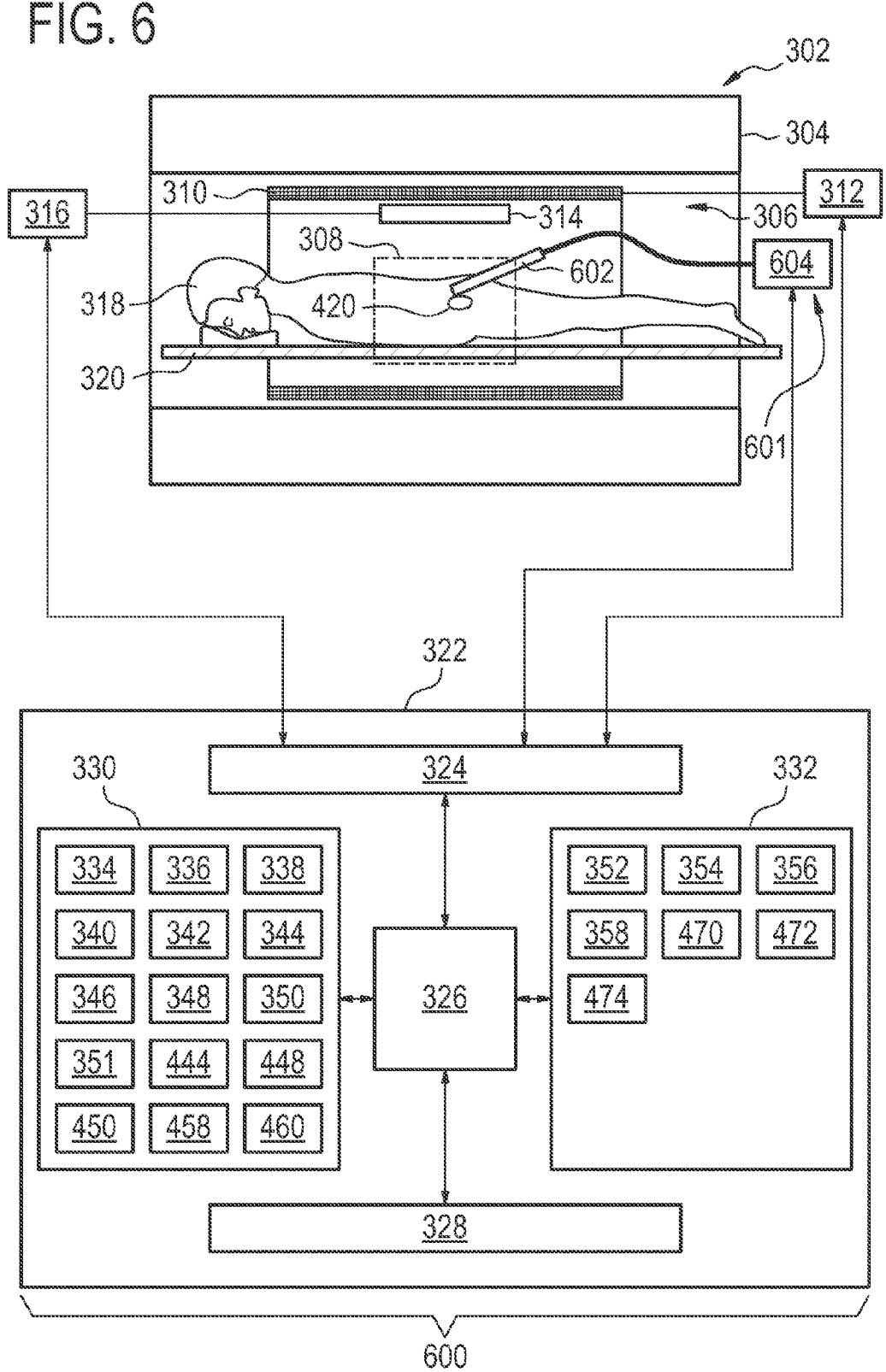
FIG. 6 shows an embodiment of a medical apparatus according to a further embodiment of the invention.

FIG. 6 shows a medical apparatus 600 according to a further embodiment of the invention. In this embodiment a thermal treatment system 601 is shown. There is an applicator 602 which has been inserted into the subject 312. Near the tip of the applicator 602 is the treatment zone 420. The thermal treatment system 602 here is representative and may be either a microwave applicator, a cryo-ablator, or a laser. The applicator 602 may be adapted for supplying microwave energy for delivering a cryogenic substance to the subject 312 or may be adapted for focusing laser light into the target zone 420. Likewise the supply system 604 may be a microwave power supply, a supply system with a cryogenic or cooling fluid, or it may be a laser power supply. The thermal treatment system 601 is shown as being connected to the hardware interface 324 of the computer system 322. The contents of the computer storage 330 and the computer memory 332 are equivalent to the embodiments shown in FIGS. 3, 4 and 5. The instructions and computer code contained therein allow the processor 326 to control the thermal treatment system 601 in a manner equivalent to the embodiments shown in FIGS. 4 and 5.

Figure 7:
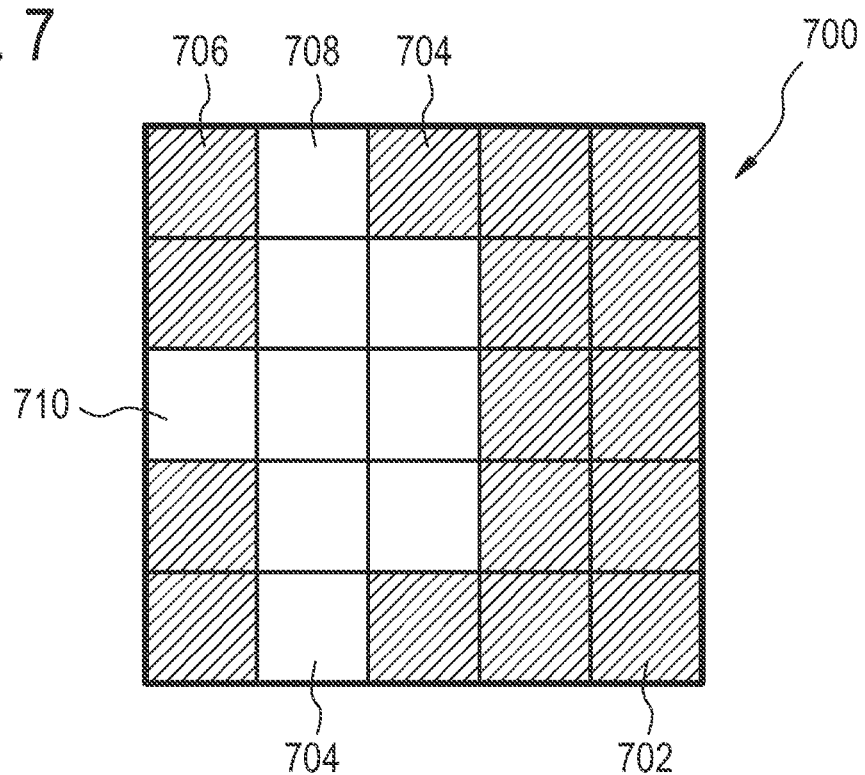
FIG. 7. shows a graph which is used to illustrate a method of extrapolating the temperature in voxels in a calibration thermal map.

FIG. 7 is a graph which is used to illustrate a method of extrapolating the temperature in voxels in a calibration thermal map 700. The calibration thermal map is divided into two types of voxels in this illustration. The voxels 702 with single hash marks are voxels which have spectroscopic temperature data. The empty voxels 704 are voxels which do not have spectroscopic temperature data. Not all voxels are labeled. Voxels 706 and 709 are both voxels with temperature data. Voxel 708 which is located between voxels 706 and 709 does not have temperature data. The simplest method of extrapolating temperature to voxels such as voxel 708 would be to perform a simple extrapolation. In this example voxel 708 could simply be the average temperature between voxels 706 and 709. Likewise voxels 710 and 704 could also have their temperature calculated in this manner. Then the remaining voxels which do not have a temperature sign could also be calculated by interpolating the temperature within.

Figure 8:
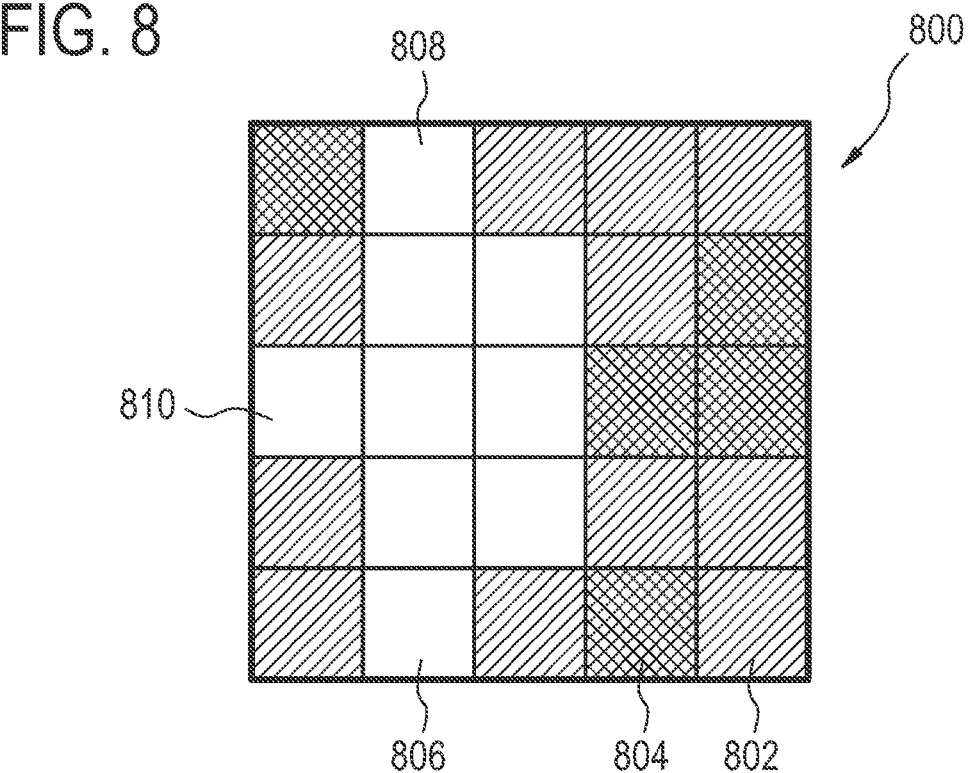
FIG. 8 is a graph which is used to illustrate a further method of extrapolating the temperature in voxels in a calibration thermal map.

FIG. 8 illustrates a more complicated method of determining the temperature of voxels within a calibration thermal map 800. In the example shown in FIG. 8 there are now three types of tissue. Voxel 802 is representative of a first tissue type, a single hashing is used. Voxel 802 is the first tissue type and voxels of this type have temperature data. Voxel 804 is representative of the second tissue type. The voxels of the second tissue type are indicated with double hashing and have temperature data also. Voxel 806 is representative of voxels of a third tissue type. For the voxels in 806 there is no temperature data which was acquired using the spectroscopic magnetic resonance data.

The temperatures of the voxels of the third tissue type 806 could be interpolated as they were in FIG. 7. However in this case the thermodynamic properties of the three tissue types 802, 804, 806 are quite different. For instance the third tissue type could be mostly fluid whereas the first tissue type may be adipose tissue and the second tissue type may be glandular tissue. The heat transfer of these three tissue types may therefore be quite different. In the example shown in FIG. 8 voxels on the boundary 806, 808 and 810 could again have their boundaries closed by using simple rules such as extrapolation or only examining heat transfer from their adjacent neighbors. The remaining voxels, instead of being interpolated could be solved for by assuming a steady state temperature within FIG. 8 and solving for the heat flow between the various voxels. This could be for instance performed by constructing a thermal model using a finite difference scheme and repeatedly calculating it until it converges to a solution. If there is a small number of voxels also a thermal lumped elements method could be used for calculating the values of the temperature in the voxels of the third tissue type 806.

FIG. 9 shows an even yet more complicated example of how a calibration thermal map could be calculated using a model. The example shown in FIG. 9 is identical with FIG. 8 except four voxels labeled 902 are also heated using a temperature treatment system according to an embodiment of the invention. The voxels in FIG. 9 were heated a known amount and known location during the acquisition of the spectroscopic magnetic resonance data. Hence a known amount of heat was added to each of these voxels 902 a finite difference scheme may be used to calculate the heat flow from these voxels into the surrounding voxels, it may be used to more accurately calculate the temperature in the voxels with the third tissue type 806.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical apparatus
302 magnetic resonance imaging system
304 magnet
306 bore of magnet
308 imaging zone
310 magnetic field gradient coils
312 magnetic field gradient coils power supply
314 radio-frequency coil
316 transceiver
318 subject
320 subject support
322 computer system
324 hardware interface
326 processor
328 user interface
330 computer storage
332 computer memory
334 spectroscopic magnetic resonance data
336 calibration thermal map
338 baseline magnetic resonance thermometry data
340 magnetic resonance thermometry data
342 spectroscopic pulse sequence
344 magnetic resonance thermometry pulse sequence
346 proton density pulse sequence
348 magnetic resonance data
350 magnetic resonance image
351 temperature map
352 control module
354 calibration thermal map module
356 temperature map module
358 image reconstruction module
400 medical apparatus
402 high intensity focused ultrasound system
404 fluid filled chamber
406 ultrasound transducer
408 mechanism
410 mechanical actuator/power supply
412 path of ultrasound
414 ultrasound window
416 gel pad
418 sonication point
420 target zone
444 treatment plan
448 temperature treatment system commands
450 pause commands
458 identified voxels
460 thermal model
470 temperature treatment system control module
472 voxel identification module
474 temperature extrapolation module
500 medical apparatus
501 radio-frequency tissue heating system
502 antenna
504 radio-frequency transmitter
600 medical apparatus
601 thermal treatment system
602 applicator
604 supply system
700 calibration thermal map
702 voxel with temperature data
704 voxel without temperature data
706 voxel with temperature data
708 voxel without temperature data
709 voxel with temperature data
800 calibration thermal map
802 voxel first tissue type (with temperature data)
804 voxel second tissue type (with temperature data)
806 voxel third tissue type (no temperature data)
808 voxel third tissue type
810 voxel third tissue type
900 calibration thermal map

The invention claimed is:

1. An apparatus comprising:
a magnetic resonance imaging system, the magnetic imaging system comprising:
a magnet,
magnetic gradient field coils, and
a radio frequency coil;
a processor for controlling the apparatus; and
a memory storing machine readable instructions for execution by the processor, wherein execution of the instructions causes the processor:
to control the magnetic resonance imaging system to generate a spectroscopic pulse sequence and in response thereto to acquire spectroscopic magnetic resonance data for an imaging zone,
to produce a calibration thermal map of the imaging zone from the acquired spectroscopic magnetic resonance data,
to control the magnetic resonance imaging system to generate a magnetic resonance thermometry pulse sequence and in response thereto to acquire baseline magnetic resonance thermometry data for the imaging zone, and
to repeatedly: control the magnetic resonance imaging system to generate the magnetic resonance thermometry pulse sequence and in response thereto to acquire additional magnetic resonance thermometry data for the imaging zone, and produce a temperature map of the imaging zone from the calibration thermal map, the baseline magnetic resonance thermometry data, and the additional magnetic resonance thermometry data.

2. The apparatus of claim 1, further comprising a temperature treatment system for treating a target volume of a subject, wherein during acquisition of the additional magnetic resonance thermometry data execution of the instructions further causes the processor to:
generate temperature treatment system commands in accordance with the temperature map; wherein the temperature treatment system commands cause the temperature treatment system to treat the target volume; and
send the temperature treatment system commands to the temperature treatment system.

3. The apparatus of claim 2, wherein execution of the instructions further causes the processor to:
generate pause commands which cause the temperature treatment system to pause treatment of the target zone for a predetermined period of time;
send the pause commands to the temperature treatment system;
re-acquire the spectroscopic magnetic resonance data during the predetermined period of time;
re-calculate the calibration thermal map using the spectroscopic magnetic resonance data; and
re-acquire the baseline magnetic resonance thermometry data.

4. The apparatus of claim 2, wherein the temperature treatment system is chosen from the group consisting of a high intensity focused ultrasound system, a radio-frequency tissue treating system, microwave applicator, a cryo-ablator, and a laser.

5. The apparatus of claim 2, wherein the temperature treatment system commands are generated in accordance with any one of the following: a treatment plan, the temperature map, and combinations thereof.

6. The apparatus of claim 1, wherein execution of the instructions further cause the processor to identify voxels of the calibration thermal map which lack spectroscopic thermal magnetic resonance data for calculating the thermal map, wherein execution of the instructions further causes the processor to extrapolate the thermal map into the identified voxels.

7. The apparatus of claim 6, wherein the thermal map is extrapolated and/or refined using a thermal model of the subject.

8. The apparatus of claim 7, wherein execution of the instructions further causes the processor to construct the thermal model using the spectroscopic magnetic resonance data.

9. The apparatus of claim 7, further comprising a temperature treatment system for treating a target volume of a subject, wherein execution of the instructions further causes the processor to treat the target volume during acquisition of the magnetic resonance thermometry data, and wherein the treatment of the target volume is modeled by the thermal model.

10. The apparatus of claim 6, wherein the thermal map is extrapolated by interpolating the temperature in the identified voxels.

11. The apparatus of claim 1, wherein the baseline magnetic resonance thermometry data and the additional magnetic resonance thermometry data is chosen from the group consisting of proton density data, T1 relaxation time data, T2 relaxation time data, T2-star relaxation time data, diffusion coefficient data, proton resonance frequency shift data, and combinations thereof.

12. The apparatus of claim 1, wherein spectroscopic magnetic resonance data is descriptive of the proton-resonance frequency shift of multiple resonance peaks.

13. The apparatus of claim 1, wherein acquiring the spectroscopic magnetic resonance data includes determining a difference between a first resonance frequency peak for water and a reference resonance frequency peak which remains substantially constant with temperature.

14. The apparatus of claim 13, wherein acquiring the baseline magnetic resonance thermometry data and the additional magnetic resonance thermometry data includes determining a temperature change in the imaging zone from a phase change between two phase images of the imaging zone at a given echo time.

15. A method of operating an apparatus including a magnetic resonance imaging system, the method comprising:
employing the magnetic resonance imaging system to generate a spectroscopic pulse sequence and in response thereto acquiring spectroscopic magnetic resonance data for an imaging zone;
producing a calibration thermal map of the imaging zone from the acquired spectroscopic magnetic resonance data;
employing the magnetic resonance imaging system to generate a magnetic resonance thermometry pulse sequence and in response thereto acquiring baseline magnetic resonance thermometry data for the imaging zone;
employing the magnetic resonance imaging system to repeatedly generate the magnetic resonance thermometry pulse sequence and in response thereto acquiring additional magnetic resonance thermometry data for the imaging zone; and
repeatedly producing a temperature map of the imaging zone from the calibration thermal map, the baseline magnetic resonance thermometry data, and the additional magnetic resonance thermometry data.

16. The method of claim 15, wherein acquiring the spectroscopic magnetic resonance data includes determining a difference between a first resonance frequency peak for water and a reference resonance frequency peak which remains substantially constant with temperature.

17. The method of claim 16, wherein acquiring the baseline magnetic resonance thermometry data and the additional magnetic resonance thermometry data includes determining a temperature change from a phase change between two phase images of the imaging zone at a given echo time.

18. The method of claim 15, wherein the apparatus further includes a therapy system, the method further comprising:
   during acquisition of the additional magnetic resonance thermometry data, the therapy system applying heating or cooling to a target volume of a subject.

19. An apparatus, comprising:
   a magnetic resonance imaging system;
   a processor for controlling the apparatus; and
   a memory storing machine readable instructions for execution by the processor, wherein execution of the instructions causes the processor to control the apparatus:
      to perform a proton spectroscopic temperature imaging mapping of the imaging zone to obtain an absolute temperature map of the imaging zone;
      subsequently to perform a series of proton resonance frequency temperature imaging mappings of the imaging zone; and
      to produce a series of temperature maps of the imaging zone from the absolute temperature map of the imaging zone and the proton resonance frequency temperature imaging mappings of the imaging zone.

20. The apparatus of claim 19, further comprising a therapy system for treating a target volume of a subject, the target volume at least partly falling within the imaging zone, wherein execution of the instructions further causes the processor:
   to generate therapy system commands in accordance with the temperature map; and
   to send the therapy system commands to the therapy system,
   wherein the therapy system commands cause the therapy system to apply one of heating and cooling to the target volume during the series of proton resonance frequency temperature imaging mappings of the imaging zone.

* * * * *